United States Patent [19]

Blackett

[11] 4,122,854

[45] Oct. 31, 1978

[54] ELECTROSURGICAL APPARATUS
[75] Inventor: John H. Blackett, London, England
[73] Assignee: Matburn (Holdings) Limited, London, England
[21] Appl. No.: 497,317
[22] Filed: Aug. 14, 1974
[30] Foreign Application Priority Data
Aug. 23, 1973 [GB] United Kingdom ............... 39991/73
[51] Int. Cl.$^2$ .............................................. A61N 3/02
[52] U.S. Cl. .................................. 128/303.13; 361/42; 361/91
[58] Field of Search ..................... 128/303.13, 303.14, 128/303.17, 303.18, 2.1 P; 317/31, 18 A, 18 B, 18 D, 18 R; 361/42, 91, 92

[56] References Cited
U.S. PATENT DOCUMENTS

| 3,513,353 | 5/1970 | Lansch | 317/31 |
| 3,601,126 | 8/1971 | Estes | 128/303.14 |
| 3,628,094 | 12/1971 | Billin | 128/2.1 D |
| 3,683,923 | 8/1972 | Anderson | 128/303.14 |
| 3,812,858 | 5/1974 | Oringer | 128/303.14 |
| 3,905,373 | 9/1975 | Gonser | 128/303.14 |

FOREIGN PATENT DOCUMENTS

| 1,139,927 | 11/1962 | Fed. Rep. of Germany | 128/303.13 |
| 855,459 | 11/1960 | United Kingdom | 128/303.17 |

Primary Examiner—Lee S. Cohen
Attorney, Agent, or Firm—William R. Liberman

[57] ABSTRACT

An electrosurgical apparatus has a monitor in the form of a voltage sensitive circuit. The circuit responds to an increase in the voltage of the apparatus to produce a control signal. The control signal operates a relay to switch off the apparatus and/or to produce an alarm signal.

6 Claims, 1 Drawing Figure

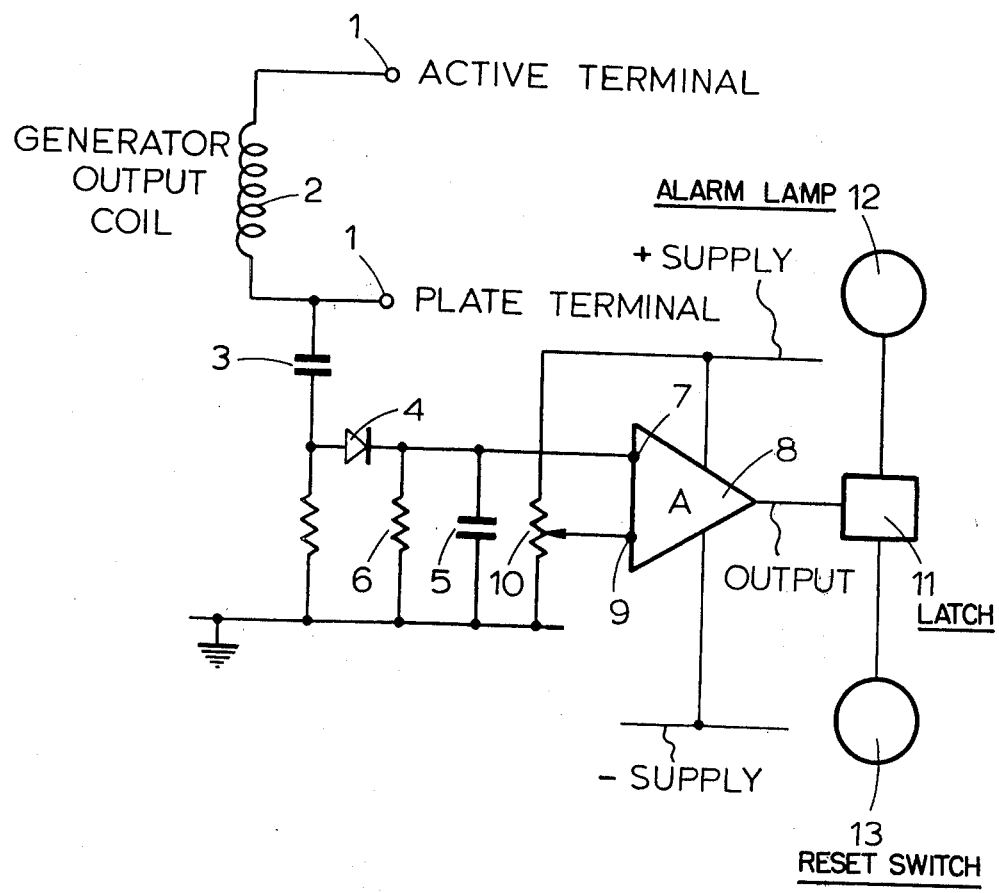

ELECTROSURGICAL APPARATUS

BACKGROUND OF INVENTION

Electrosurgical apparatus has associated with it an electric shock harzard. This is of particular concern with an electrosurgical generator where electrodes are connected directly to a patient.

With a conventional electrosurgical generator, a plate electrode is connected to earth and, therefore, connects the body of the patient directly to earth. One of the most common causes of electric shock is the passage of an electric current from a "live" source in contact with the patient to earth via the plate electrode. The "live" source may be an electrode from another piece of equipment which has become live due to a fault within the equipment.

This electric shock hazard may be prevented by isolating an output circuit of the electrosurgical generator from earth to provide a very high impedance to earth to the passage of current at the power supply frequency. However, this form of isolated output circuit itself produces a hazard in that the output of the electrosurgical generator can appear between the plate circuit and earth. This could cause burns to the patient or to any person in contact with the plate circuit when the generator is energised. The condition will occur if a low impedance path exists between the active output terminal and earth, for example if the active electrode is placed upon earthed metal.

It is well known that for safety use of an electrosurgical apparatus it is essential to ensure that the plate electrode is connected to the generator and that there is continuity throughout the connecting lead. Hitherto, it has been normal practice to include in an electrosurgical generator a monitor circuit that passes a small current through the plate electrode circuit, with a relay or similar means to detect the passage of this current if the circuit is complete. The relay can be arranged to operate an alarm if there is a loss of continuity in the plate circuit. This system has certain disadvantages, namely: (a) a twin conductor plate electrode lead is required, (b) the monitoring current can produce an electric shock hazard, (c) the monitoring current can cause interference with patient monitoring apparatus, and (d) the monitor circuit requires additional circuit components connected to the plate electrode circuit increasing the difficulty of maintaining satisfactory electrical isolation.

An object of the present invention is to provide a way of making an electrosurgical generator with an isolated output circuit, but without the hazard of diathermy burns from the plate circuit.

A further object of the invention is to eliminate the need for a plate electrode lead continuity monitor by providing an arrangement in which if the plate electrode is not connected or the lead is broken and an attempt is made to use the apparatus, the output voltage on the plate circuit will rise above the trigger level of the monitor, causing the generator to be switched off. To prevent the voltage exceeding the trigger level the plate must be connected to provide a lower capacitive impedance to earth.

BRIEF SUMMARY OF INVENTION

According to the invention there is provided an electrosurgical apparatus which has a monitor in the form of a voltage sensitive circuit which is responsive to an increase in the voltage of the apparatus with respect to earth beyond a predetermined value to produce a control signal, means responsive to the control signal being provided to switch off the apparatus and/or to produce an alarm signal.

The invention is particularly, but not exclusively, applicable to an electro-diathermy apparatus. With such an apparatus, the monitor is arranged to produce the control signal if the voltage on the diathermy plate with respect to earth rises above the predetermined value.

This control signal is used to switch off a diathermy generator and also to give alarm indications. The voltage level at which the monitor is arranged to operate should be below that when a burn can be produced and this is typically below 100 volts.

BRIEF DESCRIPTION OF ACCOMPANYING DRAWINGS

The drawing is an electrical circuit diagram.

DESCRIPTION OF A PREFERRED EMBODIMENT

In the illustrated embodiment of the invention, an electro diathermy apparatus has a monitor in the form of a voltage sensing circuit. This voltage sensing or monitor circuit is connected to an electrode circuit of the diathermy apparatus, such electrode circuit being connected with a plate electrode through terminals 1, connected with a generator output coil 2 of the electrode circuit. The connection between the monitor circuit and the electrode circuit includes a capacitor 3, the value of which is sufficiently low that it does not appreciably increase the capacitance to the electrode circuit. The capacitor 3, which may be replaced by a resistor, a miniature transformer or an optically coupled isolator, is a means by which a small part of the generator output from the electrode circuit can be transferred to the monitor circuit. The voltage sensing circuit includes a half wave rectifier circuit including a diode 4, a capacitor 5, and a resistor 6. This half wave rectifier circuit produces a direct voltage at one input 7 of an operational amplifier 8. Another input 9 to the operational amplifier 8 is taken to a variable reference voltage obtained from a potentiometer 10. The operational amplifier 10 acts as a trigger circuit as its output changes rapidly from a maximum negative voltage to a maximum positive voltage, when the voltage across the resistor 6 of the half wave rectifier circuit exceeds a reference voltage which has been predetermined by the setting of the potentiometer 10.

The signal produced by the amplifier 10 is a control signal which is supplied to a relay switching means 11. When the signal is applied to the relay 11, the relay operates to break supply of power to a diathermy generator and also to illuminate an alarm lamp 12 or to actuate an audible alarm. It is desirable that the relay switching means 11 incorporates a latch to prevent the reconnection of the supply after the input signal has fallen to zero. The latch may be either electrical or mechanical and may be reset by either the operation of a control or automatically by other means in the circuit. The apparatus is provided with a re-set switch 13 which enables the supply or power to the generator to be restored or if desired, the re-set switch can be arranged to operate automatically on removal of the fault conditions.

Instead of a relay switching means 11, a semiconductor switch (either a transistor or thyristor) may be employed.

The amplifier 8 may be certain instances be unnecessary as the power level may be sufficient to operate the switch directly.

What we claim is:

1. A radio-frequency electrosurgical device which comprises a radio-frequency generator, a power lead and a return lead, means for coupling the power lead and the return lead to the radio-frequency generator, an active electrosurgical electrode, means for coupling the power lead to the active electrosurgical electrode to power the active electrode, a passive electrode, means for coupling the passive electrode to the return lead, a high impedance connection coupling the return lead to ground at a point between the passive electrode and the ratio-frequency generator, voltage monitoring means coupled across the high impedance connection for indicating a predetermined voltage drop imposed across the high impedance connection.

2. In an electrosurgical generator circuit having a source of diathermy current connected to an active electrode and the return path for current being via a plate electrode to the source, the improvement comprising a high impedance connection between ground and the return path between the plate electrode and the source, the entire circuit, including the source, the active electrode and the plate electrode, being otherwise isolated from ground and a voltage-sensitive monitor circuit for preventing a large voltage increase across the high impedance connection, the voltage sensitive circuit comprising a rectifier, having a output and being connected between the high impedance connection and ground, and trigger circuit means connected to said rectifier output and adapted to provide a control signal when the output voltage from the rectifier exceeds a predetermined value; switch means connected to the trigger circuit means and actuated by said control signal to switch off the apparatus upon generation of a voltage greater than said predetermined value and electrical conductor means connecting the rectifier to the generator circuit at a point between the plate electrode and ground; whereby a fraction of the output of the generator circuit can be transferred to the monitor circuit and a control signal is produced when the voltage increase between the plate electrode and ground exceeds a predetermined value.

3. The apparatus of claim 2 wherein the generator circuit comprises only a single plate electrode.

4. An apparatus as in claim 2 wherein the trigger circuit means is an amplifier comprising a first input, a potentiometer connected with the first input, by which a variable reference voltage can be applied to the first input, and a second input of the said amplifier being connected to the rectifier, such that the amplifier output is rapidly changeable from a maximum negative voltage to a maximum positive voltage when the said reference voltage has been exceeded, thereby to produce a signal which actuates the switch means.

5. The apparatus of claim 4 wherein the conductor means for placing the monitor and the generator circuit electrodes in electrical connection comprises a capacitor.

6. An apparatus as claimed in claim 4, also having means to prevent the switch means being re-activated after it has been actuated by a signal from the trigger circuit means.

* * * * *